United States Patent [19]

Donnan et al.

[11] Patent Number: 4,596,573

[45] Date of Patent: Jun. 24, 1986

[54] CONTAINER

[75] Inventors: Jeremy F. Donnan; David A. Reed, both of Nottinghamshire, England

[73] Assignee: The Boots Company p.l.c., England

[21] Appl. No.: 566,353

[22] Filed: Dec. 28, 1983

[30] Foreign Application Priority Data

Jan. 8, 1983 [GB] United Kingdom ................. 8300475

[51] Int. Cl.[4] ................................................ A61M 5/00

[52] U.S. Cl. ............................ 604/415; 128/DIG. 24

[58] Field of Search .................. 604/415, 408; 222/83, 222/85; 128/DIG. 24

[56] References Cited

U.S. PATENT DOCUMENTS 3,509,879 5/1970 Bathish et al. ...................... 604/408
3,788,374 1/1974 Saijo .
4,187,893 2/1980 Bujan ................................. 604/408
4,198,972 4/1980 Herb ................................... 604/408
4,234,026 11/1980 Bayham .
4,365,629 12/1982 Pert et al. ................... 128/DIG. 24
4,439,192 3/1984 Leurink ........................... 604/415 X

FOREIGN PATENT DOCUMENTS 8204398 12/1982 PCT Int'l Appl. .
1544811 4/1979 United Kingdom .
2045207 10/1980 United Kingdom .

*Primary Examiner*—Stephen C. Pellegrino
*Attorney, Agent, or Firm*—Jacobs & Jacobs

[57] ABSTRACT

A container suitable for storing and dispensing parenteral fluids comprises a flat member 2 inserted into a pouch 1 of plastics material. The member has two ports 9, 10 passing therethrough which are protected by removeable tabs 14, 15 having passageways 19, 20 which are coaxial with the ports. The port 9 is sealed after filling by a cup-shaped closure (25, FIG. 4 not shown). The port 10 is closed by a ruptureable membrane and may have a resilient plug (29, FIG. 5 not shown) and needle guide (30, FIG. 5 not shown). The tabs may be connected to the member by portions 16, 16*a*, 17, 17*a* and 18 of reduced thickness. The outer ends of the passageways are sealed by covers 21, 22 or by flattening and sealing the ends of the passageways.

The member, ports and tabs may be integrally formed by injection moulding (FIG. 1).

21 Claims, 13 Drawing Figures

CONTAINER

This invention relates to flexible containers suitable for the storage and dispensing of parenteral liquids.

The present invention provides a container having two ports and comprising a flexible pouch comprising two sheets of a medically-acceptable plastics material which are joined along their side edges and at one end thereof, the other end thereof comprising at least one substantially flat member carring the ports which communicate between the interior of the pouch and the exterior of the container, said ports being integrally formed with the member and having integrally formed removable tabs which are intended to protect the outermost ends of the ports. The tabs may be joined to the member by areas of reduced thickness to facilitate the removal of the tabs to expose the outer ends of the ports. Preferably each port is provided with a tab which can be removed individually to expose the outer end of the port. The tabs may have passageways extending therethrough coaxial with the ports to enable the one port to be used for filling and for a resilient plug and, if present, a needle guide to be inserted into the other port as will be described hereinafter. After filling the outer ends of the passageways may be sealed by applying a cover or by flattening the outer end of the passageway and sealing the flattened surfaces. One member may extend partially or completely across the width of the other end of the pouch and may comprise the two ports or two members may be provided each containing one port.

One of the two ports is used to fill the container and may be sealed after filling by inserting a cup-shaped closure the base of which forms a ruptureable membrane. The other of the two ports also has a ruptureable membrane which may be integrally formed with the port or may be formed by the base of a cup-shaped closure in a similar way to that described above. The other port contains a resilient plug located outwardly of the membrane to minimise egress of the contents of the container after the membrane has been punctured and may contain a needle guide to ensure that any needle used to puncture the membrane is directed centrally. The needle guide may comprise a cylindrical body having an axial bore and the outer ends of the bore may be flared to facilitate correct insertion of the needle.

The invention will be illustrated by the following description of several embodiments thereof. The description is given by way of example only and has reference to the accompanying drawings in which.

Figure 1:
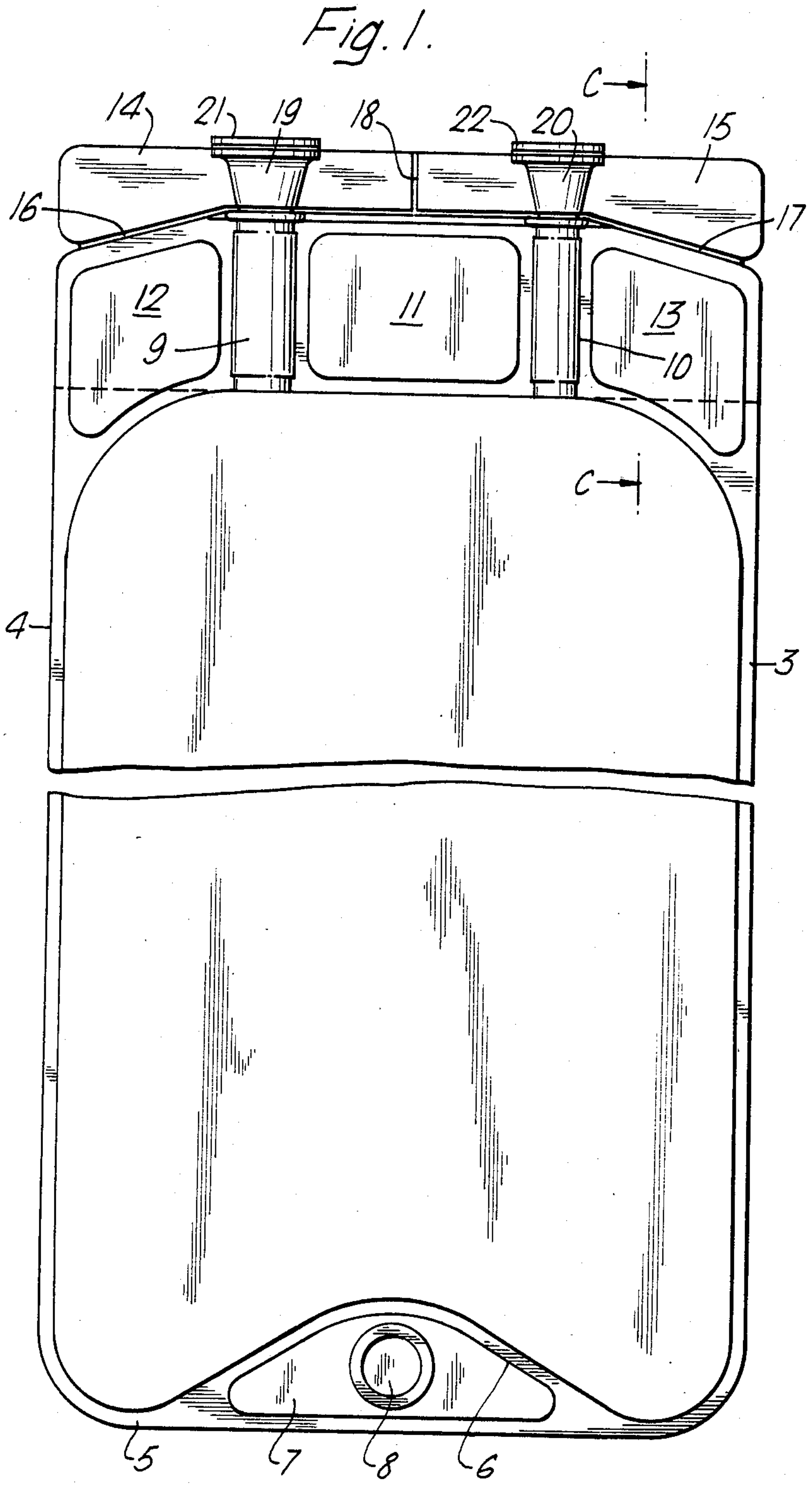
FIG. 1 is a plan view of a flexible container according to the present invention.
Figure 2:
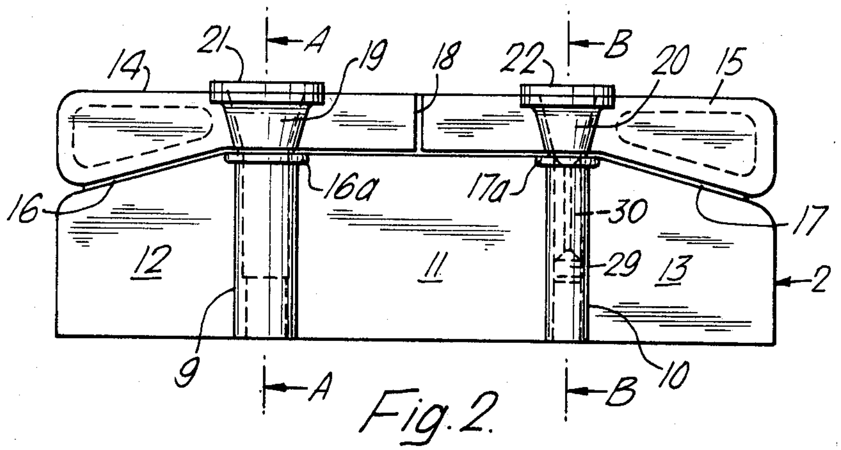
FIG. 2 is a plan view of a component for a flexible container similar to that shown in FIG. 1.
Figure 4:
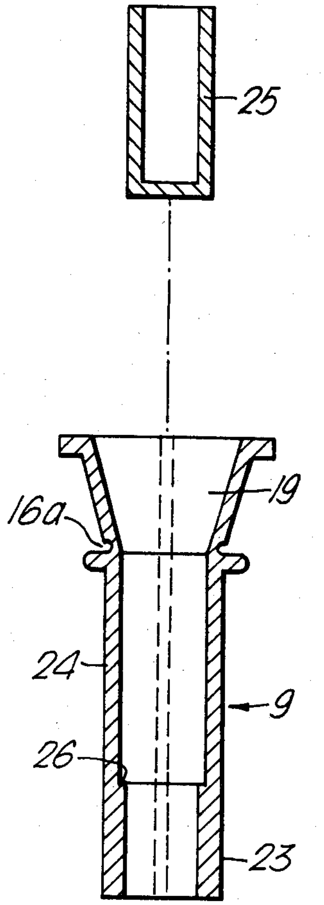
FIG. 4 is an exploded cross-sectional view taken along the line A—A of FIG. 2 or FIG 3.
Figure 8A:
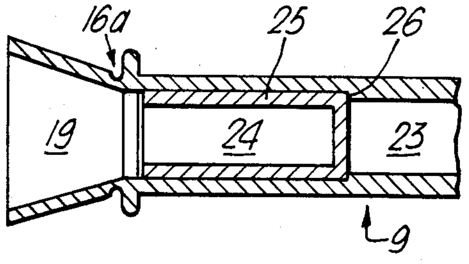
Figure 8B:
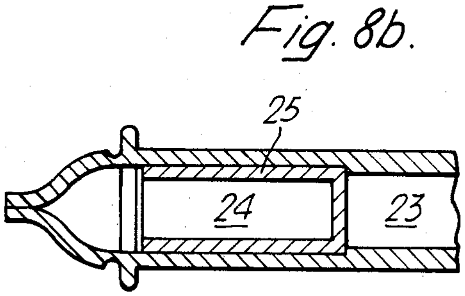
Figure 9:
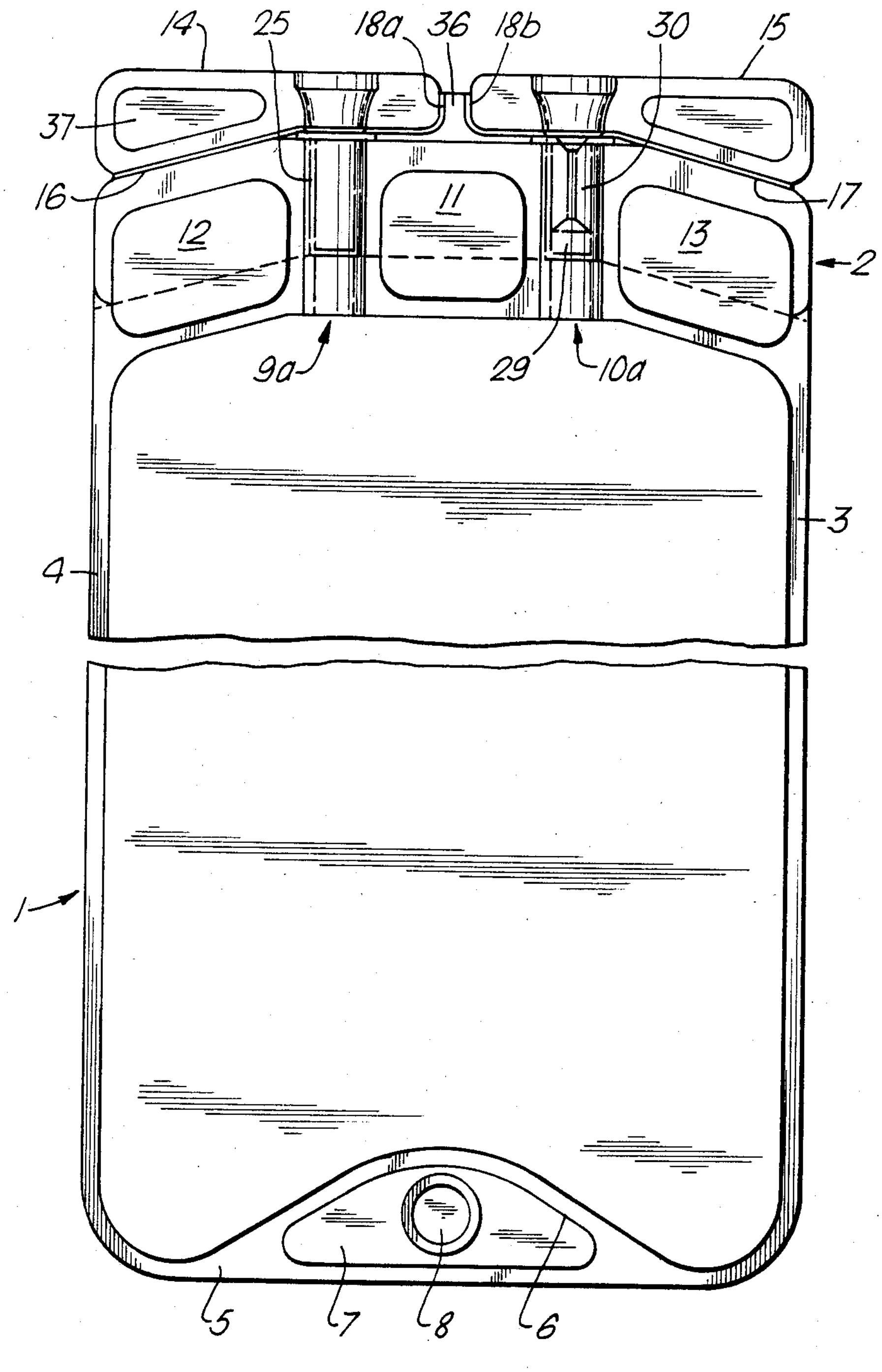
Figure 10:
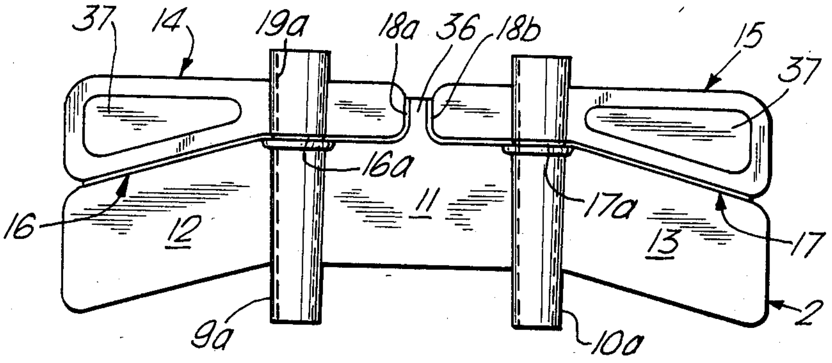
Figure 11A:
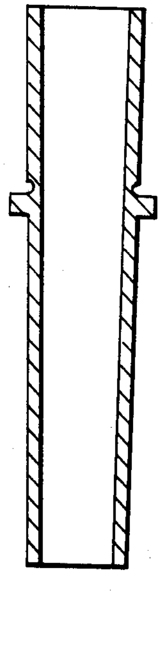
Figure 11B:
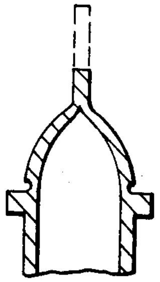

FIGS. 8*a* and 8*b* are cross-sectional views of a portion of the component illustrated in FIG. 4 showing diagrammatically one method of sealing the passageways after filling;

FIG. 9 is a plan view similar to FIG. 1 but illustrating a further embodiment;

FIG 10 is a view similar to that of FIG. 2 illustrating the further embodiment shown in FIG. 9 in which the ports have not been sealed, and FIGS. 11*a* and 11*b* are views similar to FIGS. 8*a* and 8*b* but of the further embodiment illustrated in FIG. 9.

In FIG. 1 is shown a flexible container which is substantially flat in its unfilled state and which comprises a pouch 1 manufactured from a medically acceptable plastics material and a member 2 moulded from a medically acceptable plastics material which closes the open end of the pouch 1. The pouch 1 may be manufactured from two sheets of the plastics material which are joined together along their edges 3, 4 and at one end 5 for example by welding. Alternatively the two sheets may be formed from the so-called "lay-flat" tubing which is sealed at the one end 5. If required the lay-flat tubing may also be welded along the edges 3, 4. The one end of the pouch 1 is sealed in such a way that means are provided whereby the container can be suspended with the one end 5 uppermost in use. In the embodiment shown in FIG. 1 a second weld line is provided to surround a flat portion 7 through which a hole 8 is punched so that, in use, the container may be suspended by the hole 8.

The synthetic plastics material from which the pouch 1 is manufactured may be any material which is suitable for use in contact with the fluids used in medical treatment (for example plasticised polyvinylchloride, ethylene-vinyl acetate co-polymers, biaxially oriented polypropylene). Alternatively the pouch may be manufactured from laminated or co-extruded medically acceptable plastics materials.

The member 2 is moulded for example by injection moulding techniques from a material which is medically acceptable (for example plasticised polyvinylchloride, ethylene-vinyl acetate co-polymers or polypropylene co-polymers) and which is capable of being joined to the material of the pouch 1 in any suitable manner. The member 2 comprises two ports 9, 10 separated by a web 11. Planar flanges 12, 13 extend outwardly from the ports 9, 10 in the same plane as the web 11. The flanges 12, 13 extend to the full width of the pouch 1. The member 2 also comprises two removeable tabs 14, 15 which are connected to the web 11 and flanges 12, 13 by relatively thin sections 16, 17 of the member which are easily broken to enable the tabs to be removed from the member 2. To enable the tabs to be removed individually a further relatively thin section 18 is provided between the tabs 14, 15. Each tab 14, 15 has a frusto-conical paasageway 19, 20 formed integrally therewith. The smaller diameter ends of these passageways 19, 20 are coaxial with the ports 9, 10 respectively. At the junction of the ports 9, 10 and the passageways 19, 20 there are sections of reduced thickness 16*a*, 17*a* to facilitate removal of the tabs 14, 15. The large diameter ends of the passageway are sealed by covers 21, 22. These covers are applied after filling the container as will be described hereinafter.

The ports 9, 10 will now be described in more detail. The port 9 as shown in FIG. 4 is tubular and of circular cross-section. That part 23 of the bore of the port 9 which is directed into the container is of smaller diameter than that part 24 of the bore which communicates with the passageway 19. When the container is assembled prior to filling the bore of the port 9 is not obstructed but after filling a cup-shaped closure 25, the base of which forms a ruptureable membrane, is inserted and sealed into the larger diameter part 24 of the bore to seal the container as will be described hereinafter. As the closure is inserted to its correct position it contacts the shoulder 26 formed where the two parts 23, 24 of the bore meet.

Figure 5:
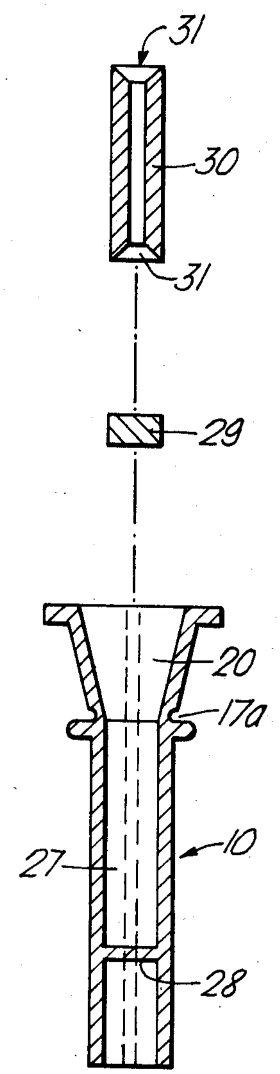
FIG. 5 is an exploded cross-sectional view taken along the line B—B of FIG. 2 or FIG. 3.

The port 10 as shown in FIG. 5 is tubular and of circular cross-section. The bore 27 is occluded by a membrane 28 which is integrally-molded as the member 2 is formed. The membrane 28 is of such a thickness that it can be punctured by a needle and is preferably of a resilient material so that when the needle is removed the puncture hole tends to close to prevent egress of the contents of the container. The port 10 is intended to be used to add additional materials such as medicaments to the contents of the container. To prevent leakage of any liquid which does escape through the puncture hole the portion of the bore 27 of the port 10 located outward of the membrane 28 receives a resilient plug 29 which is a friction fit in the bore and which is sufficiently resilient to seal any puncture hole made therethrough by a needle. The plug 29 may be cylindrical as shown in FIG. 5 or it may be spherical prior to insertion and may be squashed after insertion to seal the port 10. So that the needle punctures the plug and membrane centrally a needle guide 30 is inserted outward of the plug 29. The needle guide 30 is tubular and has a central bore of sufficient diameter to enable a needle to pass easily therethrough. The outermost ends 31 of the bore are flared to facilitate the correct insertion of the needle. Both ends are flared to as to obviate the need to orientate the needle guide before insertion. The needle guide may conveniently be made from a harder synthetic plastics material than the member 2. Polycarbonate and unplasticised polyvinyl chloride are examples of suitable synthetic plastics materials from which the needle guide 30 may be fabricated. In an alternative embodiment (not shown) the needle guide may be provided with a contoured outer surface so that the needle guide is positioned more securely within the port 10. For example the ends of the outer surface of the needle guide may be provided with shoulders.

In an alternative embodiment (not shown) the port 10 of the member 2 is identical to the port 9 as described above and is sealed after filling by a cup-shaped closure similar to that described above by reference numeral 25. The plug 29 and needle guide 30 are then inserted into the interior of the closure as described above.

Figure 3:
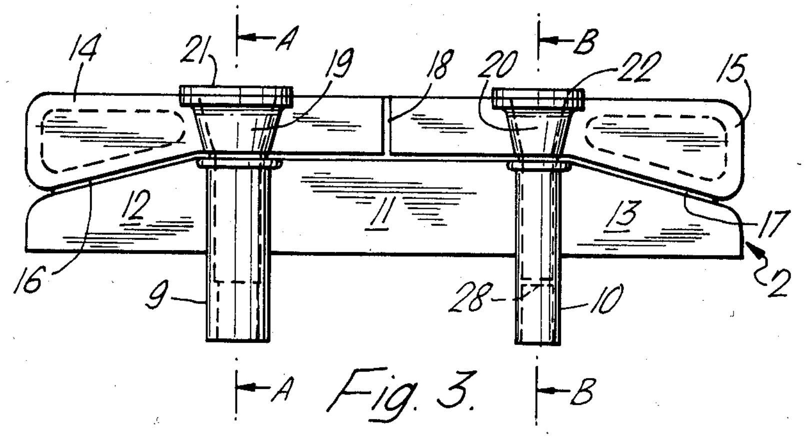
FIG. 3 is a view similar to that of FIG. 2 of an alternative embodiment.

The web 11 and flanges 12, 13 may extend the full length of the ports 9, 10 as shown in FIG. 2 or the innermost ends of the ports 9, 10 may extend into the interior of the container as shown in FIG. 3.

In a further embodiment illustrated in FIGS. 9 and 10 the member 2 carries two ports **9*a*, 10*a* which taper towards the interior of the bag as shown in FIG. 10*a*. In FIGS. 9, 10 11*a* and 11*b* the components which have already been described are identified by the same reference numerals as used herinbefore. In FIGS. 9 and 10 the tabs 14 and 15 are joined at their central edges to a central projection 36 by relatively thin sections 18*a* and 18 *b*. The provision of a central projection 36 minimises the risk that, during the removal of one of the tabs, the integrity of the sterile seal formed by the other of the tabs is jeopardised. The embodiment of FIG. 9 has apertures 37 in the tabs 14, 15 to facilitate the removal of the tabs. Similar apertures may be provided in the embodiments illustrated in FIGS. 2 and 3** as shown by the dotted lines in those Figures.

To further facilitate the removal of the tabs 14, 15 the flanges 12, 13 may be provided with apertures to enable the user to obtain a firmer grip. Alternatively the outer surfaces of the flanges or the material forming the pouch which covers them may be patterned or roughened to provide a firmer grip.

Figure 6:
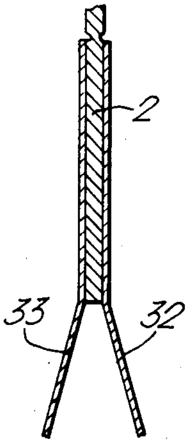
Fig. 6 is a part cross-section taken along the line C—C of FIG. 1.
Figure 7:
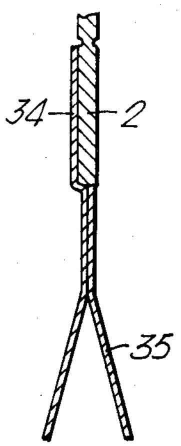
FIG. 7 is a view similar to that of FIG. 6 showing an alternative embodiment.

After the member 2 has been formed the unfilled container is assembled. The member 2 is placed between the sheets of plastics material or inside the "lay-flat" tubing and the end 5 of the pouch, and, if required, the edges 3, 4 of the pouch are sealed. Simultaneously the sheets or tubing are sealed to the member 2 to provide the container. The sheets or tubing may be sealed to the member 2 by, for example, (a) sealing the sheets 32, 33 on opposite faces of the member 2 as shown in FIG. 6 or (b) by sealing one sheet 34 to one face of the member 2 and sealing the other sheet 35 to the sheet 34 below the member 2 as shown in FIG 7.

After the container has been formed it is filled with liquid via the port 9. After filling the closure 25 is inserted into the port 9 and sealed therein for example by radio frequency welding and if required a similar closure is inserted into the port 10. The plug 29 and needle guide 30 are then inserted into the port 10 and the covers 21, 22 are placed over the passageways 19, 20 respectively.

As an alternative to the use of the covers 21, 22 the larger diameter end of the passageways 19, 20 may be flattened and sealed as shown in FIGS. **8*a* and 8*b* which show the passageway 19 on the port 9 before and after such treatment. In a similar manner the tapered ports 9*a*, 10*a* illustrated in FIG. 10 may be flattened and sealed as is depicted in FIGS. 11*a* and 11*b*. In this latter case the portion of the sealed passageway shown in FIG. 11*b*** by dotted lines is removed after sealing.

After filling the container and its contents may be sterilised, for example, by heat sterilisation. The filled container may be overwrapped by a material which minimises the loss of contents of the container by diffusion through the material of the container either before or after sterilisation.

In use the tab 14 is removed by breaking the relatively thin sections 16 and 18 or **18*a* to expose the port 9. A spike, connected to a giving set which is used to administer the contents of the container to a patient, is inserted into the port 9 and ruptures the base of the closure 25. The container may then be suspended by the aperture 8 to permit the contents to be dispensed. If it is desired to add a medicament to the contents of the container the tab 15 is removed in a similar manner to that described above to expose the outer end of the needle guide 30. The medicament may then be added for example from a syringe by passing the needle through the bore of the needle guide 30, the plug 29** and into the container.

When the tabs 14, 15 are in a position prior to use the outermost ends of the ports 9, 10 are maintained in a sterile environment. Removal of the tabs 14, 15 provides access to the ports in a convenient manner which minimises the possibility of the user touching and contaminating the outer ends of the ports. If the member 2 is manufactured by injection moulding techniques the thickness of the thin sections 16, **16*a*, 17, 17*a*, 18, 18*a* and 18*b* can be controlled so that the tabs 14, 15** can be easily removed when necessary but cannot be removed inadvertently. The presence of the member at said other end of the container enables the user to maintain a grip on the container when manipulating the tabs.

We claim:

1. A container for parenteral liquids comprising
a pouch comprising two sheets of medically-acceptable plastics material which are joined together along their edges and at one end thereof,
a substantially flat member located between and joined to the said sheets at the other end of the pouch to enclose the interior of the container, said substantially flat member having two integrally-formed ports adapted to communicate between the interior of the pouch and the exterior of the container,
the first of said ports being adapted to be sealed after the container has been filled by the insertion of a cup-shaped closure,
the second of said ports having rupturable occluding means which prevent the passage of liquid from the interior of the pouch to the exterior of the container,
removable portions integrally formed with the substantially flat member, said removable portions having passageways coaxial with the ports,
frangible webs of reduced thickness between the removable portions and the remainder of the substantially flat member to facilitate the removal of the removable portions from the substantially flat member,
the outermost ends of the passageways being adapted to be sealed after filling to protect the outermost ends of the ports.

2. A container as claimed in claim 1 wherein the rupturable occluding means in the second of said ports comprises a membrane integrally formed with the port.

3. A container as claimed in claim 2 wherein the second of said ports is provided with a resilient plug located outwardly of the membrane to minimise egress of the contents of the container after the membrane has been punctured.

4. A container as claimed in claim 3 wherein the second of said ports is provided outwardly of the resilient plug with a needle guide comprising a cylindrical body which is a push fit in the port and which has an axial bore the outermost end of which is flared.

5. A container as claimed in claim 1 wherein the rupturable occluding means comprises the base of a cup-shaped closure inserted into the port.

6. A container as claimed in claim 5 wherein the second of said ports is provided with a resilient plug located outwardly of the base of the cup shaped closure to minimise egress of the contents of the container after the membrane has been punctured.

7. A container as claimed in claim 6 wherein the second of said ports is provided outwardly of the resilient plug with a needle guide comprising a cylindrical body which is a push fit in the port and which has an axial bore the outermost end of which is flared.

8. A container containing parenteral liquid comprising
a pouch comprising two sheets of medically-acceptable plastics material which are joined together along their edges and at one end thereof,
a substantially flat member located between and joined to the said sheets at the other end of the pouch to enclose the interior of the container, said substantially flat member having two integrally-formed ports adapted to communicate between the interior of the pouch and the exterior of the container,
a cup-shaped closure sealed into the first of said ports after the container has been filled,
the second of said ports having rupturable occluding means which prevent the passage of liquid from the interior of the pouch to the exterior of the container,
removable portions integrally formed with the substantially flat member, said removable portions having passageways coaxial with the ports,
frangible webs of reduced thickness between the removable portions and the remainder of the substantially flat member to facilitate the removal of the removable portions from the substantially flat member,
the outermost ends of the passageways being sealed after filling by flattening and sealing the outermost ends of the passageways.

9. A container as claimed in claim 8 wherein the rupturable occluding means in the second of said ports comprises a membrane integrally formed with the port.

10. A container as claimed in claim 9 wherein the second of said ports is provided with a resilient plug located outwardly of the membrane to minimise egress of the contents of the container after the membrane has been punctured.

11. A container as claimed in claim 10 wherein the second of said ports is provided outwardly of the resilient plug with a needle guide comprising a cylindrical body which is a push fit in the port and which has an axial bore the outermost end of which is flared.

12. A container as claimed in claim 8 wherein the rupturable occluding means comprises the base of a cup-shaped closure inserted into the port.

13. A container as claimed in claim 12 wherein the second of said ports is provided with a resilient plug located outwardly of the base of the cup shaped closure to minimise egress of the contents of the container after the membrane has been punctured.

14. A container as claimed in claim 13 wherein the second of said ports is provided outwardly of the resilient plug with a needle guide comprising a cylindrical body which is a push fit in the port and which has an axial bore the outermost end of which is flared.

15. A container containing parenteral liquid comprising
a pouch comprising two sheets of medically-acceptable plastics material which are joined together along their edges and at one end thereof,
a substantially flat member located between and joined to the said sheets at the other end of the pouch to enclose the interior of the container, said substantially flat member having two integrally-formed ports adapted to communicate between the interior of the pouch and the exterior of the container,
a cup-shaped closure sealed into the first of said ports after the container has been filled,
the second of said ports having rupturable occluding means which prevent the passage of liquid from the interior of the pouch to the exterior of the container,
removable portions intergrally formed with the substantially flat member, said removable portions having passageways coaxial with the ports,
frangible webs of reduced thickness between the removable portions and the remainder of the substantially flat member to facilitate the removal of the removable portions from the substantially flat member, the outermost ends of the passageways being sealed after filling by covers over the outermost ends of the passageways.

16. A container as claimed in claim 15 wherein the rupturable occluding means in the second of said ports comprises a membrane integrally formed with the port.

17. A container as claimed in claim 16 wherein the second of said ports is provided with a resilient plug located outwardly of the membrane to minimise egress of the contents of the container after the membrane has been punctured.

18. A container as claimed in claim 17 wherein the second of said ports is provided outwardly of the resilient plug with a needle guide comprising a cylindrical body which is a push fit in the port and which has an axial bore the outermost end of which is flared.

19. A container as claimed in claim 15 wherein the rupturable occluding means comprises the base of a cup-shaped closure inserted into the port.

20. A container as claimed in claim 19 wherein the second of said ports is provided with a resilient plug located outwardly of the base of the cup shaped closure to minimise egress of the contents of the container after the membrane has been punctured.

21. A container as claimed in claim 20 wherein the second of said ports is provided outwardly of the resilient plug with a needle guide comprising a cylindrical body which is a push fit in the port and which has an axial bore the outermost end of which is flared.

* * * * *